(12) United States Patent
Burkhart et al.

(10) Patent No.: US 7,803,173 B2
(45) Date of Patent: Sep. 28, 2010

(54) LOOPED HIGH STRENGTH SUTURE CHAIN FOR KNOTLESS FIXATION

(75) Inventors: Stephen S. Burkhart, San Antonio, TX (US); R. Donald Grafton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 848 days.

(21) Appl. No.: 11/392,798

(22) Filed: Mar. 30, 2006

(65) Prior Publication Data

US 2006/0259076 A1    Nov. 16, 2006

Related U.S. Application Data

(60) Provisional application No. 60/666,518, filed on Mar. 30, 2005.

(51) Int. Cl.
*A61B 17/04* (2006.01)
*A61B 17/84* (2006.01)

(52) U.S. Cl. .......... 606/232; 606/228; 606/300

(58) Field of Classification Search ......... 606/228, 606/232, 300; 623/13.11, 13.14, 13.19, 13.2
See application file for complete search history.

(56) References Cited

U.S. PATENT DOCUMENTS

| 4,946,377 | A | | 8/1990 | Kovach | |
|---|---|---|---|---|---|
| 5,500,000 | A | * | 3/1996 | Feagin et al. | 606/232 |
| 5,891,168 | A | | 4/1999 | Thal | |
| 6,045,574 | A | * | 4/2000 | Thal | 606/232 |
| 6,143,017 | A | * | 11/2000 | Thal | 606/232 |
| 6,319,271 | B1 | * | 11/2001 | Schwartz et al. | 606/232 |
| 7,357,810 | B2 | * | 4/2008 | Koyfman et al. | 606/232 |
| 2003/0130694 | A1 | * | 7/2003 | Bojarski et al. | 606/228 |
| 2004/0193217 | A1 | * | 9/2004 | Lubbers et al. | 606/232 |
| 2004/0204722 | A1 | * | 10/2004 | Sikora et al. | 606/151 |
| 2005/0283156 | A1 | * | 12/2005 | Schmieding et al. | 606/72 |

FOREIGN PATENT DOCUMENTS

WO     WO 96/17544     6/1996

* cited by examiner

*Primary Examiner*—Julian W Woo
(74) *Attorney, Agent, or Firm*—Dickstein Shapiro LLP

(57) ABSTRACT

A chain of loops of braided high strength suture for surgical applications. The suture chain is advantageous for use in knotless fixation of soft tissue to bone, and can be used for knotless side-to-side suturing of U-shaped defects, such as rotator cuff tears.

7 Claims, 13 Drawing Sheets

LOOPED HIGH STRENGTH SUTURE CHAIN FOR KNOTLESS FIXATION

CROSS-REFERENCE TO RELATED APPLICATIONS

This application claims the benefit of U.S. Provisional Application Ser. No. 60/666,518, filed on Mar. 30, 2005, the entire disclosure of which is incorporated by reference herein.

BACKGROUND OF THE INVENTION

1. Field of the Invention

The present invention relates to surgical fixation and, more particularly, to knotless tissue fixation using a chain-like serial suture loop construct.

2. Description of the Related Art

Securing suture during surgery can be difficult and demanding. Various suture constructs have been developed in an effort to avoid the need to tie knots in suture, particularly during arthroscopic surgery. For example, U.S. Pat. No. 6,143,017 to Thal discloses tissue fixation using a free-standing continuous suture loop snagged by an anchoring device. While it appears that tissue can be bound to bone according to the Thal teachings, it is not evident how to accomplish in situ surgical refinements such as adjustment of the loop length or tension on the repaired tissue. Technology for knotless tissue fixation would benefit from further development.

SUMMARY OF THE INVENTION

The present invention provides apparatus and methods for knotless tissue fixation using serial suture loop constructs. The construct preferable includes at least two loops formed of high strength suture. The suture loop constructs allow for surgical fixation of tissue without the need to tie knots. The loops are captured with anchoring implants. Tension on the fixation can be refined in situ by selecting which loops to capture.

The present invention also provides a method of forming a chain of suture loops for surgical application. The chain of suture loops can be formed in the normal fashion, i.e., as a series of interlinked, non-intersecting loops. Alternatively, the chain can be formed of a series of intersecting loops, with at least one of the loops or "links" of the chain formed by first "piercing" or "lacing" an end of the suture through a standing part of the suture, to form an initial suture "intersection" in a first direction, for example in the x-y direction. The suture intersection is then locked by lacing the end through the suture intersection in a second direction, for example in the z direction, piercing both strands at the center of the initial junction, and pulling the strands tight. Successive loops or links may be developed along the length of suture in similar fashion to form a suture chain.

The present invention also provides a method for knotless fixation of anatomical tissue during surgical applications by employing a chain of suture loops. The method comprises the steps of: (i) providing a construct that includes at least two loops formed of and connected by suture; and (ii) surgically fixating the anatomical tissue using the suture loop construct without tying knots.

The present invention further provides a method of tensioning suture used for knotless fixation of anatomical tissue during surgical applications. The method includes the steps of: (i) providing a suture chain that includes at least two loops formed of high strength suture; (ii) securing an end of the suture chain to a fixation device; and (iii) pulling on the other end of the suture chain to tension the suture chain.

Other features and advantages of the present invention will become apparent from the following description of exemplary embodiments of the invention with reference to the accompanying drawings.

DETAILED DESCRIPTION OF THE INVENTION

Figures 1, 2, 3, 4:
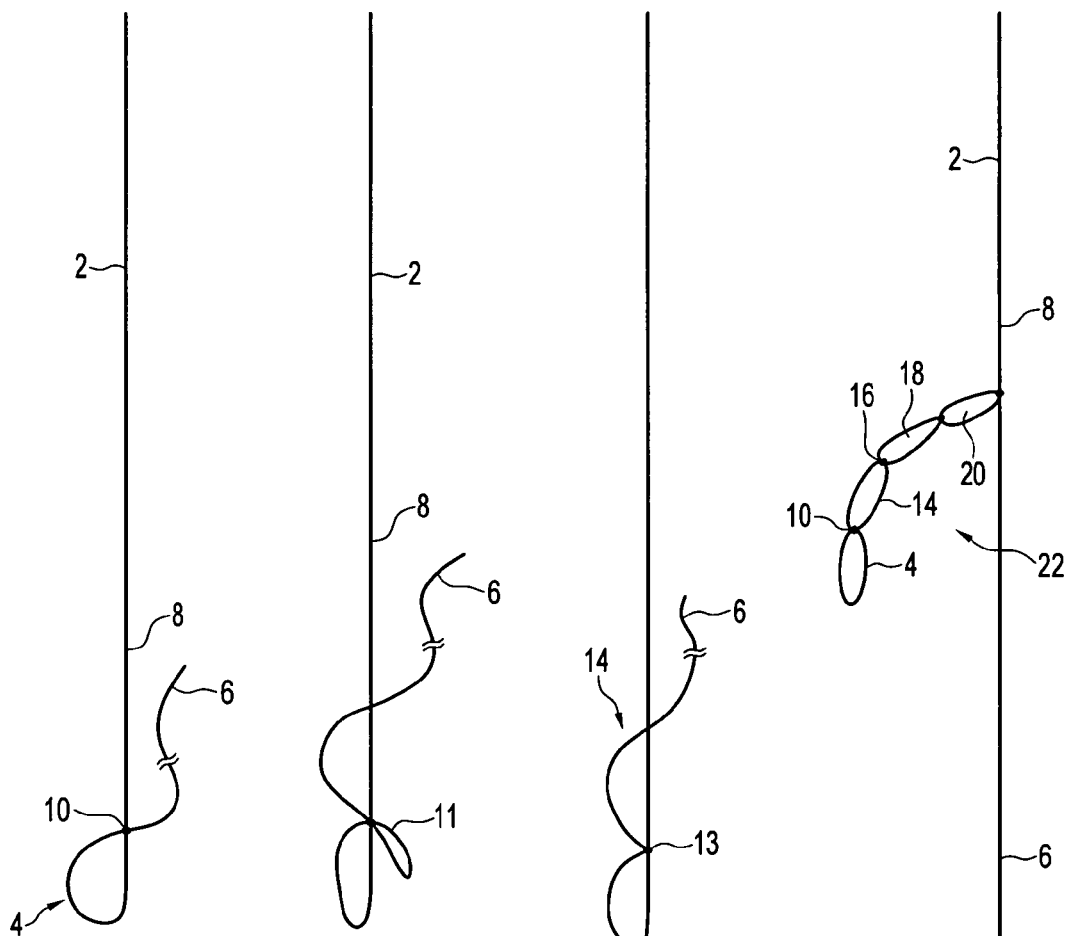
FIG. 1 illustrates an initial stage of chained suture loop formation according to the present invention.
FIG. 2 illustrates locking a suture loop and initial formation of an adjacent loop on the chain according to the present invention.
FIG. 3 illustrates formation of the adjacent loop of the chained suture loops according to the present invention.
FIG. 4 illustrates a completed suture loop chain according to the present invention.

The present invention provides apparatus and methods for knotless tissue fixation using serial suture loop constructs. The construct preferable includes at least two loops of suture, preferably high strength suture. The suture loop constructs allow for surgical fixation of tissue without the need to tie knots. The loops are captured with anchoring implants or similar devices.

The invention also provides a method of forming a chain of suture loops, preferably of braided high strength suture loops, for surgical applications. As described in more detail below, the suture chain can comprise a series of closed loops of suture formed in a conventional "chain." Alternatively, at least one of the loops or "links" of the chain can be formed first by "piercing" or "lacing" an end of the suture through a standing part of the suture, to form an initial suture "intersection" in a first direction (for example, in the x-y direction). The suture intersection is then locked by lacing the end through the suture intersection in a second direction (for example, in the z direction), piercing both strands at the center of the initial junction, and pulling the strands tight. Successive loops or links may be developed along the length of suture in similar fashion to form a suture chain.

Suture loop constructs according to the present invention are referred to as "chains" in this application. The term "chain" is used in the specification and claims to refer to exemplary embodiments of the invention. A "chain" in this context refers broadly to a construct including a series of loops. The loops can be, but need not be, interlinked. In this manner, the term "chain" as used in this application includes, but need not be limited to, the commonly understood definition in which links or rings are fitted into one another. Rather, the chains of the present invention can include two or more loops that are connected together.

Each loop preferably has a fixed perimeter. The suture can be interlaced, rather than knotted, as described further below, to establish and maintain loop geometry. Preferably, all loops are similar in size.

In an exemplary embodiment, high-strength suture is utilized, such as the high strength suture sold by Arthrex, Inc. of Naples, Fla. under the tradename FiberWire, which is disclosed and claimed in U.S. Pat. No. 6,716,234, the entire disclosure of which is incorporated herein by reference.

FiberWire suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire suture includes a core within a hollow braided construct, the core being a twisted yarn of UHMWPE. The suture may optionally include filaments of various colors.

Suture chains of the present invention incorporating advanced, high strength materials, such as FiberWire suture, can be used in demanding orthopedic applications such as shoulder repairs. The suture chains of the present invention offer surgeons practical means for creating suture constructs of adjustable size without having to tie a knot in situ.

Referring now to the drawings, where like elements are designated by like reference numerals, FIG. 1 illustrates a length of suture 2 at an initial stage of suture chain formation according to one embodiment of the present invention. A first suture loop 4 is formed by lacing suture 2 through itself at least once, preferably at least twice. Using a 0.029" or smaller needle, for example, loop 4 is started by lacing a bitter end 6 of the suture 2 between filaments of a standing part 8 of suture 2 to establish a junction 10. Thus, junction 10 is formed initially as a four-way intersection of suture 2 laced through itself.

Junction 10 is sufficient to establish a suture loop, and the present invention includes looped constructs formed in the above manner. It is preferable, however, to "lock" the junction 10 to establish a fixed size. The junction 10 can be locked in various ways, including wrapping junction 10 with suture, tying a knot around junction 10, or by applying adhesive to junction 10.

Figure 5:
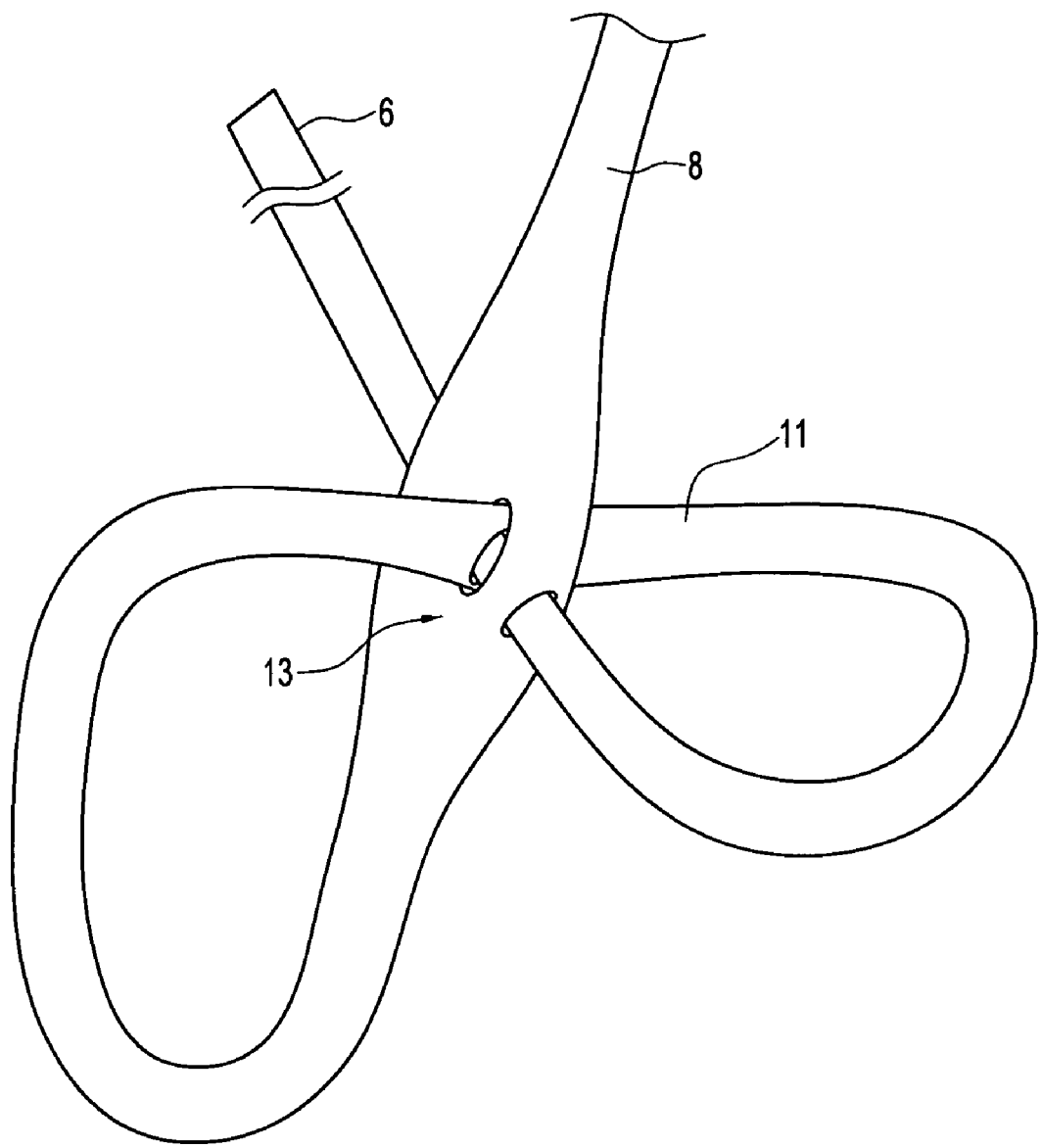
FIG. 5 provides an enlarged depiction of suture loop formation according to an exemplary embodiment of the present invention.

In an exemplary embodiment of the present invention, junction 10 is locked by lacing the suture through itself again, as follows: Referring to FIGS. 2 and 3, bitter end 6 again is laced (using a needle, not shown) through the previously-interlaced standing parts 8, 11 of suture 2 at junction 10. As a result, a six-way intersecting junction 13 of suture 2 is formed. Locking of the twice-interlaced junction 13 is completed by pulling suture 2 tight, as shown in FIG. 3. FIG. 5 is an enlarged view of junction 13 prior to tightening.

FIG. 3 also shows initial development of a second suture loop 14 formed by lacing bitter end 6 through standing part 8 of suture 2 to form a two-way junction 16 similar to junction 10. The junction 16 is locked as described above for the first loop 4. The second loop 14 preferably is the same size as the first loop 4.

Referring to FIG. 4, the steps described above are repeated to produce additional loops 18, 20. Thus, a chain of suture loops 22 is formed with four loops 4, 12, 18, 20. Suture loop chain 22 can have fewer or more than the four loops shown in FIG. 4. Although shorter chains, having two or three loops, often are preferred for working arthroscopically, the appropriate length will be determined as required by the intended application.

Alternative methods of forming a chain of suture loops without tying knots is described as follows: The junction 10 is formed by crossing suture 2 over or under the standing part 8. The bitter end 6 is then passed through the two overlapping portions of suture to secure the loop. The resulting junction is less stable than the twice interlaced junction 13 achieved by the method first described above, however. As a further alternative, various knots known to those of skill in the art could be used alone, or could be combined with interlacing as described above, to form any or all of the loops. Fixed loops are preferred, although an adjustable loop construct could be provided within the bounds of the teachings of the present invention. Twice-interlaced junctions, such as those first described above in connection with junction 13, are most preferred. These junctions maintain the loop geometry well, present a smoother outer surface, and may involve less suture weakening than do knots.

Figure 5A:
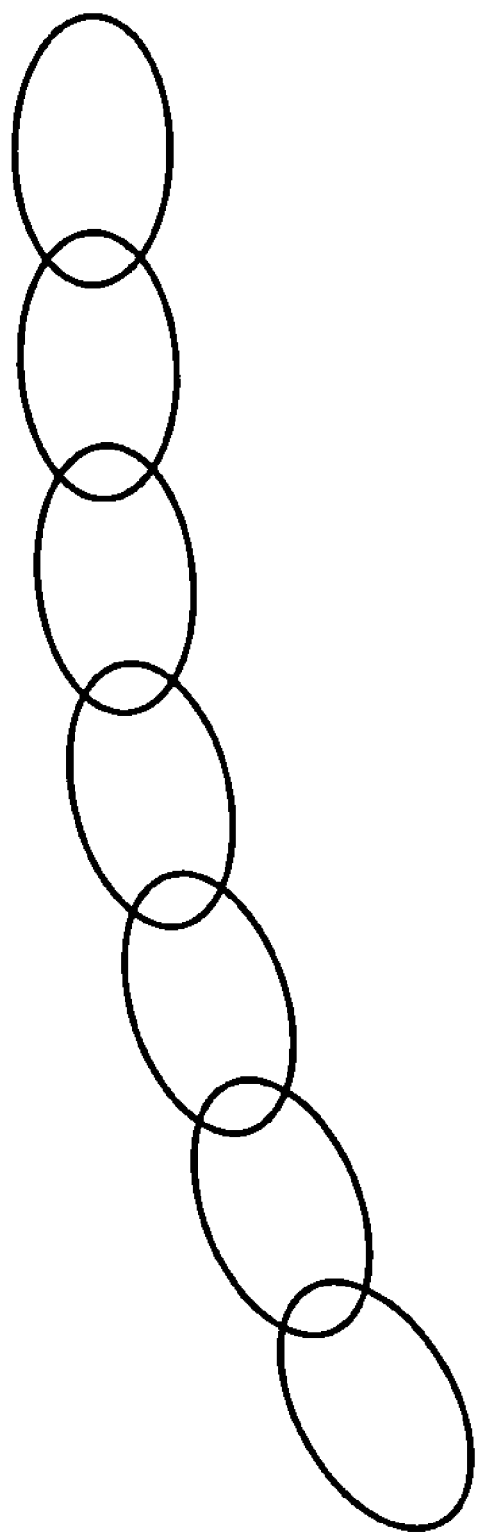
FIG. 5A shown a suture chain of the present invention is a conventional configuration of a series of interconnected loops.

Alternatively, as shown in FIG. 5A, the suture chain of the present invention can simply comprise a series of interconnected suture loops, in the more conventional "chain" configuration.

Figure 6:
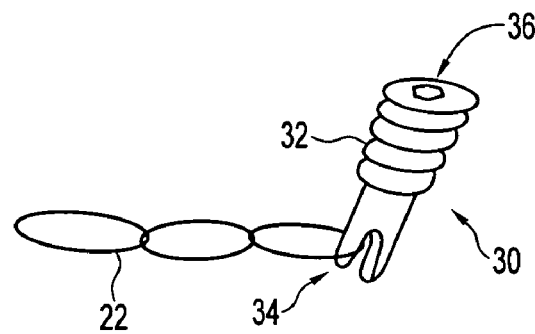
FIG. 6 illustrates a press-in suture chain anchor according to the present invention.
Figure 7:
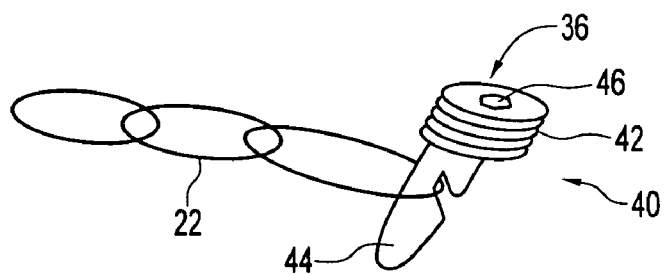
FIG. 7 illustrates an alternative suture chain anchor of the present invention.
Figure 8:
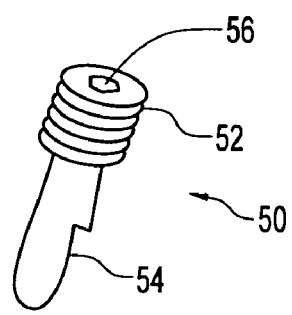
FIG. 8 illustrates a third alternative suture chain anchor according to the present invention.

The suture chains of the present invention can be used in a variety of surgical procedures, and most preferably are used to approximate tissue, for example, to approximate torn tendons to bone. FIGS. 6-8 illustrate examples of bone anchors used to secure one or more suture chains to bone in accordance with the present invention. In FIG. 6, a forked suture anchor 30 has a threaded body 32. A loop of the suture chain 22 is hooked between tines of forked tip 34. The anchor 30 is installed into bone using a hex driver received in hex socket 36, for example.

FIG. 7 illustrates a notched suture chain anchor 40 having a threaded body 42, a tip 44 notched on one side, and a hex socket 46. A loop of suture chain 22 is shown captured in the side notch. Although an end loop is shown here as the one being captured, the invention is not so limited. FIG. 8 illustrates a shouldered suture chain anchor 50 having a threaded body 52, a shouldered tip 54, and a hex socket 56. Alternatively, each of the anchors 30, 40, 50 can be provided with a tip 34, 44, 54 that is rotatably attached to its respective body 32, 42, 52, as described further below. Other types of bone anchors can also be used, without limitation. Although threaded anchors are shown, swivel anchors (described below) or press-in anchors such as the Arthrex Push-Lock™ anchor described in U.S. Patent Application Publication No. 2004/0093031, the disclosure of which is incorporated by reference herein, can be used as well. Also, rather than capturing a loop with the anchor, the chain of loops can be threaded through the eye of a needle or bone anchor, for example. The use of a bone anchor also is not necessary to utilizing suture chains of the present invention.

Figure 9:
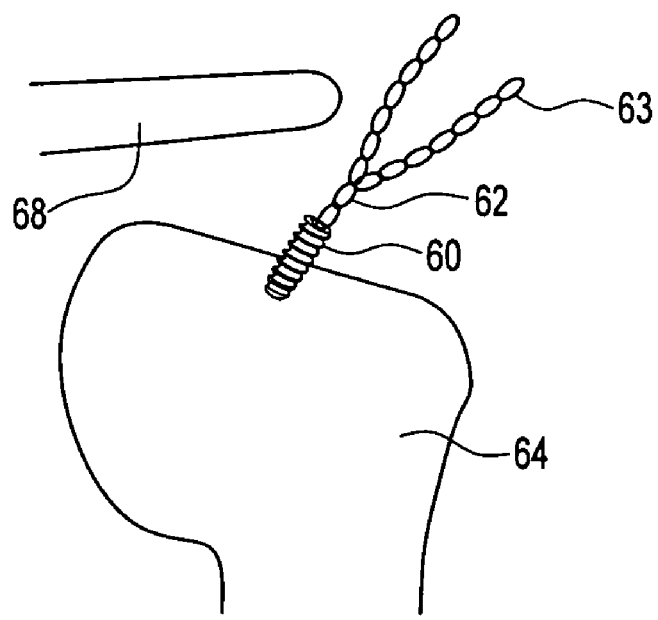
FIG. 9 depicts an initial step in shoulder repair using a double-row technique according to the present invention.
Figure 10:
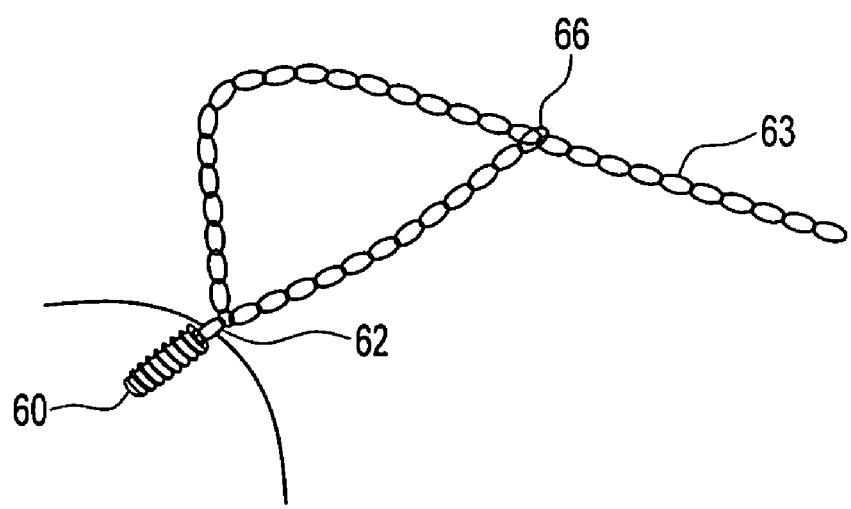
FIG. 10 depicts a step of securing the suture chain to the bone anchor according to the present invention.
Figure 11:
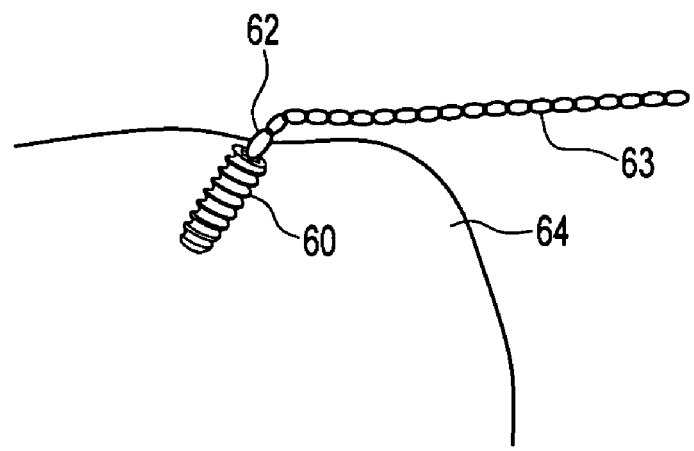
FIG. 11 depicts a step of tightening the suture chain onto the bone anchor according to the present invention.

Method steps of tissue fixation according to an exemplary embodiment of the present invention are depicted schematically in FIGS. 9-14. Referring initially to FIG. 9, a suture anchor 60 (for example, an Arthrex Biocorkscrew™, disclosed in U.S. Patent Application Publication No. 2004/0106950) having an eyelet 62 and loaded with a single or double strands of suture chain 63 is installed in bone 64. As shown in FIG. 10, with the suture chain 63 threaded through eyelet 62 of suture anchor 60, one end of suture chain 63 is passed through a loop, such as the last loop 66, of suture chain 63. Referring to FIG. 11, suture chain 63 is tightened so that link 66 is drawn adjacent eye 62 of anchor 60, and a single suture chain leg 63 extends from eyelet 62 of anchor 60.

Figure 12:
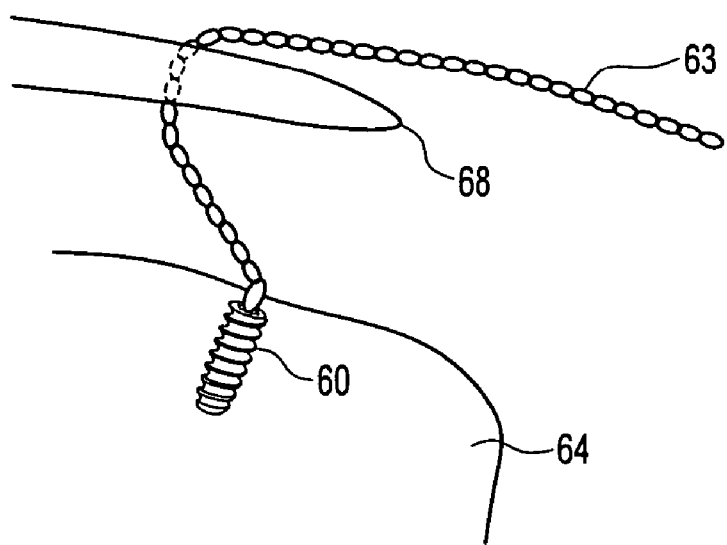
FIG. 12 depicts a step of passing the suture chain through a tendon to be reattached to bone according to the present invention.
Figure 13:
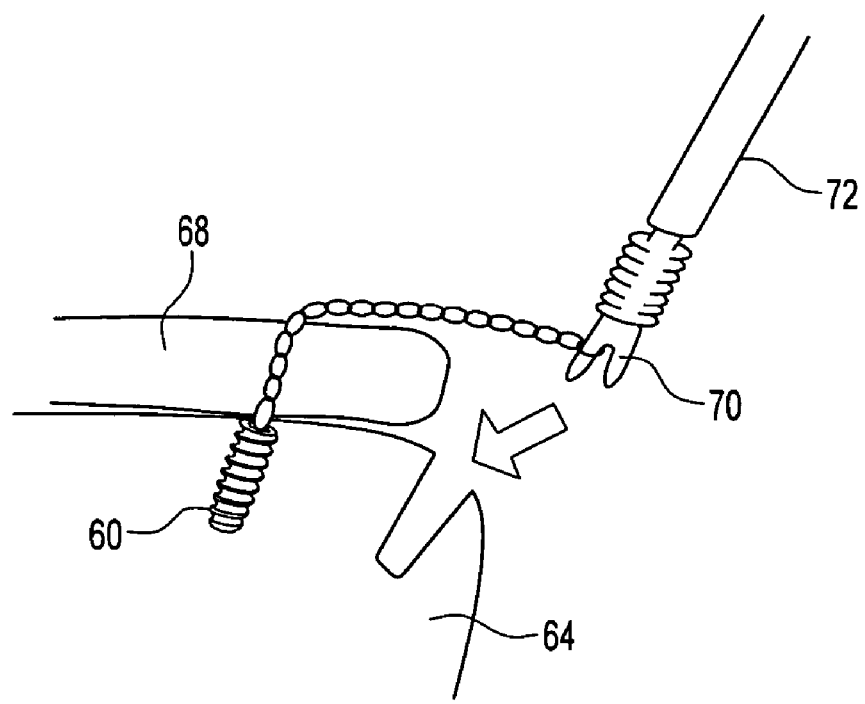
FIG. 13 depicts a step of ligament fixation by installing a suture chain anchor according to the present invention.
Figure 14:
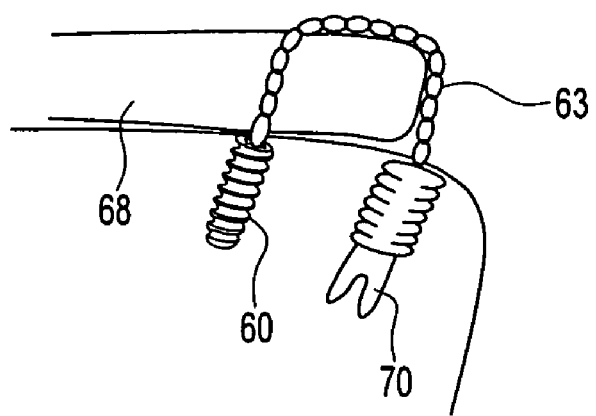
FIG. 14 depicts a completed ligament repair using a suture chain according to the present invention.

Referring next to FIG. 12, once the suture anchor has been inserted, suture chain 63 is passed through tendon 68. As shown in FIG. 13, tissue 68 is approximated to bone 64 using a second suture anchor 70. In an exemplary embodiment, second suture anchor 70 is installed using a driver 72 into a preformed opening in bone 64, with a selected loop of suture chain 63 having been captured (on the prong of the anchor) to provide the desired tension on the finished construct, shown in FIG. 14. Assorted bone anchors 60, 70 could be substituted for suture chain anchors 60, 70. The suture anchor may be an Arthrex Swivel-Lock™ (swivel suture anchor) described below, or an Arthrex Push-Lock™ anchor. Alternatively, the suture chain passed through the tissue can be secured using a single anchor. In addition, various anchors, such as those noted above and others, may be used interchangeably with only slight variations in the above procedure. For example, the suture chain can be secured by capturing two of the chain loops in forked tines prior to insertion of the anchor or anchors.

Further, regular suture may be used in addition to the suture chains of the present invention. In this case, the first suture anchor 60 will be pre-loaded with regular suture (like the current Arthrex BioCorkscrew™ or Arthrex BioCorkscrew-FT™, disclosed in U.S. Ser. No. 11/224,060). In this exemplary embodiment, the technique is similar to the one described above, except that the lateral fixation is accomplished by capturing the suture limbs (rather than chain-links) in the fork of the Swivel-Lock and tensioning the suture as the Swivel-Lock is placed. This relies on interference fixation of the suture between the anchor and the bone.

Greater fixation may be achieved by twisting the suture limbs before inserting the anchor. For the suture chain of the present invention, tension is adjusted simply by choosing to capture a different link. That is, a link is chosen and pushed to the bottom of the bone socket by the driver. If the soft tissue is not firmly held against bone, the inserter is withdrawn and a more proximal link is chosen. This gives great freedom to adjust the tension in the system.

Figure 15:
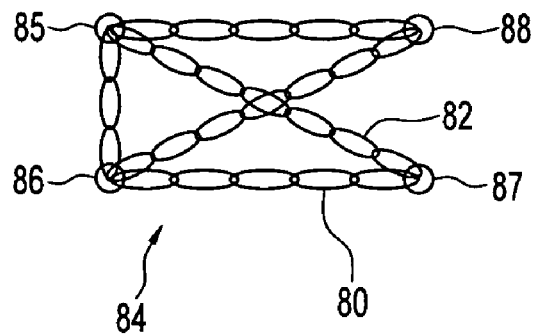
FIG. 15 illustrates a shared-load fixation using a suture chain according to the present invention.

Suture chains disclosed herein also can be used to increase the footprint of a repair and to share repair loading. Referring to FIG. 15, suture chain(s) 80, 82 are depicted in a construct fixing a section of tissue 84 to underlying bone (not shown). Using two lengths of suture chain (the second length 82 could be separately formed, or an extension of suture chain 80) provides load sharing and increases the construct footprint. Suture chains 80, 82 can be secured to bone by lacing the suture chains 80, 82 through tissue 84 at points 85, 86, 87, 88 in various patterns using four or fewer bone anchors.

Figure 16:
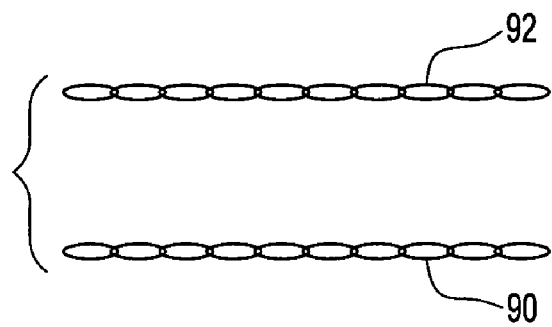
FIG. 16 illustrates an unacceptably loose tissue approximation using a suture chain construct of the present invention.
Figure 17:
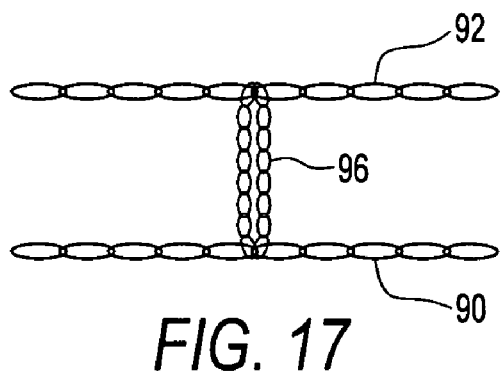
FIG. 17 illustrates a method of tightening the loose suture chain approximation according to the present invention.

Referring to FIG. 16, two suture chains 90, 92 are attached through tissue 94 to underlying bone (not shown) in a tissue-approximating construct. Suture chains 90, 92 have unacceptable laxity. Referring to FIG. 17, a length of suture chain 96 is looped around suture chains 90, 92, or through individual loops of suture chains 90, 92 to tighten the construct.

Figure 18:
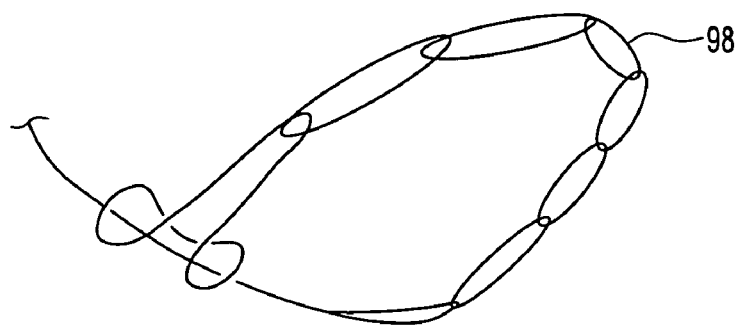
FIG. 18 illustrates a self-tightening suture chain configuration featuring an auxiliary disk anchoring device according to the present invention.
Figure 19:
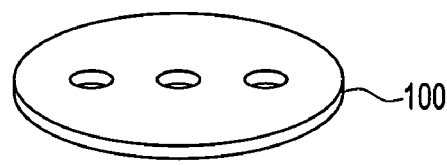
FIG. 19 illustrates a swivel suture loop anchor according to the present invention.

Other options for utilizing the suture chains of the present invention will become apparent to those of ordinary skill in the art. Referring to FIG. 18, for example, a self-tightening configuration in which suture chain 98 has been looped around itself is illustrated. Referring to FIG. 19, surface contact area of a suture chain construct can be expanded by threading a suture chain through a biocompatible disk 100. Single or multiple holes can be formed through disk 100 for accepting lengths of suture chain. The disk can be oblong to allow insertion through a narrow connection. This invention is not limited to a disk, per se. The invention includes other configurations such as rods or rectangles that will perform a similar function.

Figure 20:
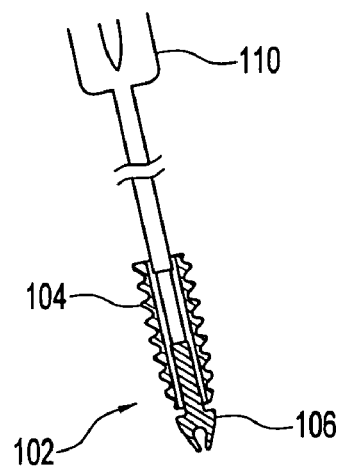
FIG. 20 illustrates a step in shoulder repair according to the present invention.
Figure 21:
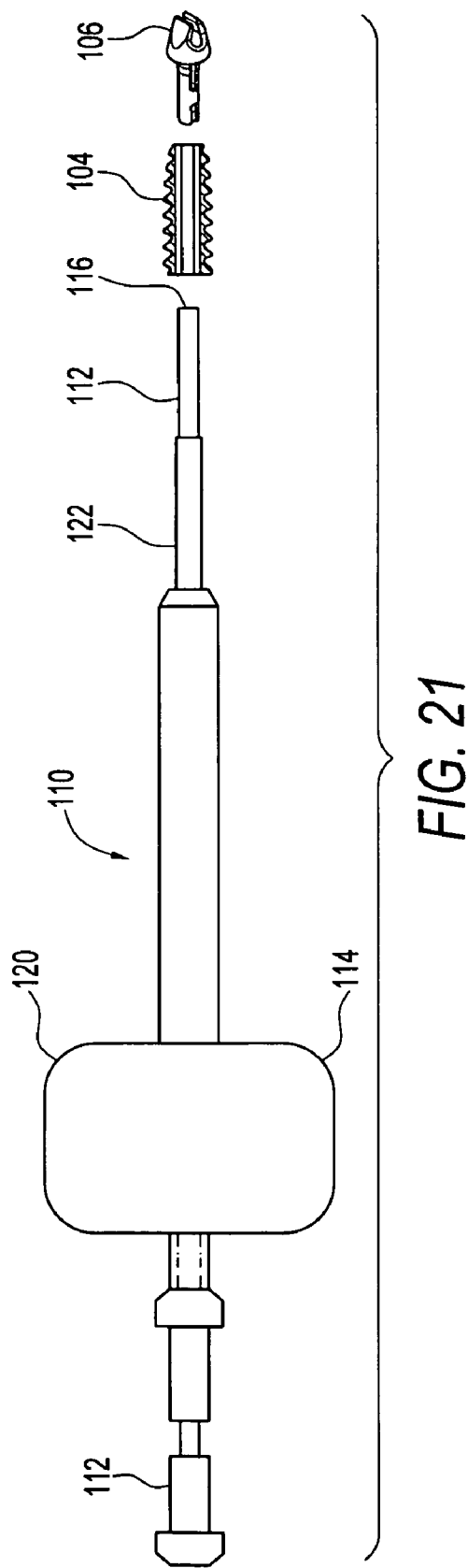
FIG. 21 is an exploded view of a two-part driver for the swivel suture chain anchor shown in FIG. 18.

Referring to FIGS. 20 and 21, another exemplary embodiment of the invention will be described in which a suture anchor 102 for securing a suture chain to bone features a swivel connection between a threaded body 104 and a detachable forked tip 106 (Swivel-Lock™ or swivel anchor). The rotatable attachment of forked tip 106 to threaded body 104 enables rotational insertion of anchor 102 without excessive twisting and knotting of a suture chain hooked by forked tip 106. Tip 106 also may be detachable from body 104 to allow greater flexibility during surgical procedures, as described further below.

Referring more specifically to FIG. 21, a driver 110 is used to install anchor 102. Driver 110 features a thin rod 112 passing slidably and rotatably through a cannulated driver assembly 114. The tip 116 of thin rod 112 is threaded internally to accept external threads 118 formed on forked tip 106. Other means of engagement between rod 112 and tip 106 can be utilized, such as a snap fit. Thin rod 112 maintains the rotational position of the tip 116 during insertion. Driver assembly 114 features a handle 120 at one end and an operative end 122 configured to engage anchor body 104.

Figure 22:
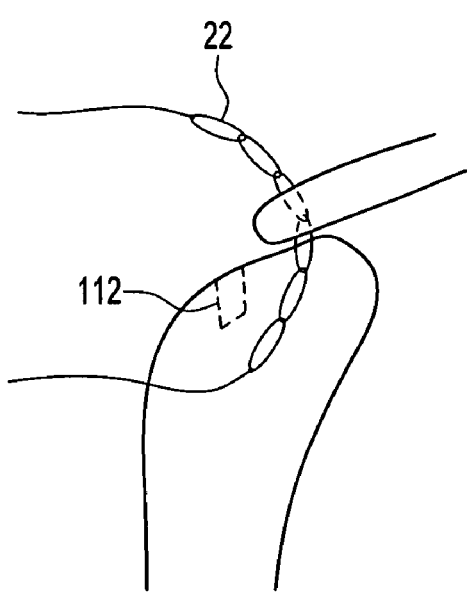
FIG. 22 illustrates a further step in shoulder repair according to the present invention.
Figure 23:
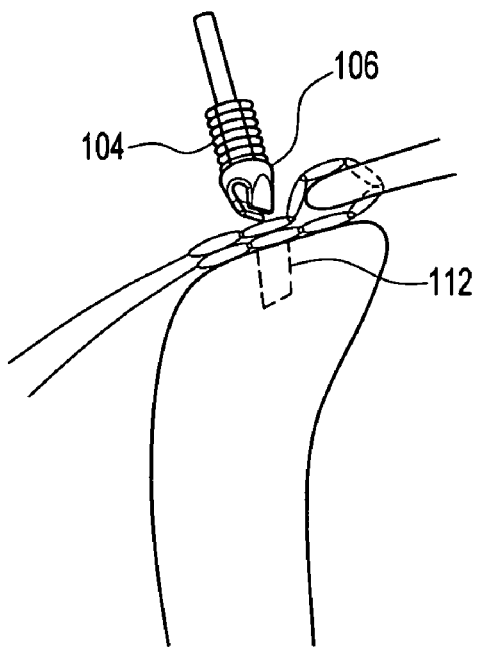
FIG. 23 illustrates a step in shoulder repair according to the present invention.
Figure 24:
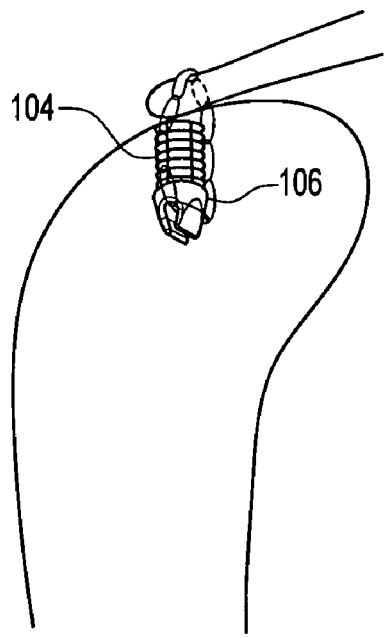
FIG. 24 illustrates a completed shoulder repair according to the present invention.

Referring in addition to FIGS. 22-24, during installation of swivel anchor 102, anchor body 104 is assembled onto operational end 122 of the driver 110. Anchor tip 106 is threaded or otherwise attached onto the tip of thin rod 112. The forked anchor tip 106 is used to capture a suture chain 22 for installation into a pre-drilled hole in bone. Suture chain 22 has been laced through a shoulder ligament as shown in FIG. 22. Advantageously, the forked tip 106 can be inserted and retrieved from the pre-drilled hole 112 (FIG. 23) prior to installation of anchor body 104. Thus, adjustments to the tension on the suture chain can be made as necessary by changing the loop of the chain 22 captured by the forked anchor tip 106.

Once an appropriate construct is determined, the forked tip 106 and captured suture chain are held in place in the pre-drilled hole in bone by rotational insertion of threaded anchor body 104 as shown in FIG. 24. Forked tip 106 preferably is configured to engage with threaded anchor body 104 such that the two fit together in axial alignment. Alternatively, the tip 106 and the body 104 can be configured to experience a snap fit when the two pieces of suture chain anchor 102 engage during installation. As explained above, the swivel suture anchor 102 may be employed as one of the two suture anchors 60, 70 in the method of knotless fixation described with reference to FIGS. 9-14.

Figure 25A:
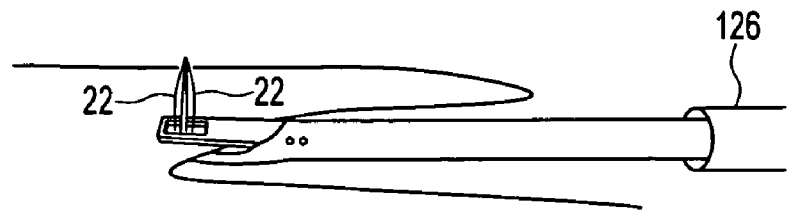
FIGS. 25A to 25G illustrate a method of knotless side-to-side suturing of U-shaped soft tissue defects using the suture chain of the present invention.
Figure 25B:
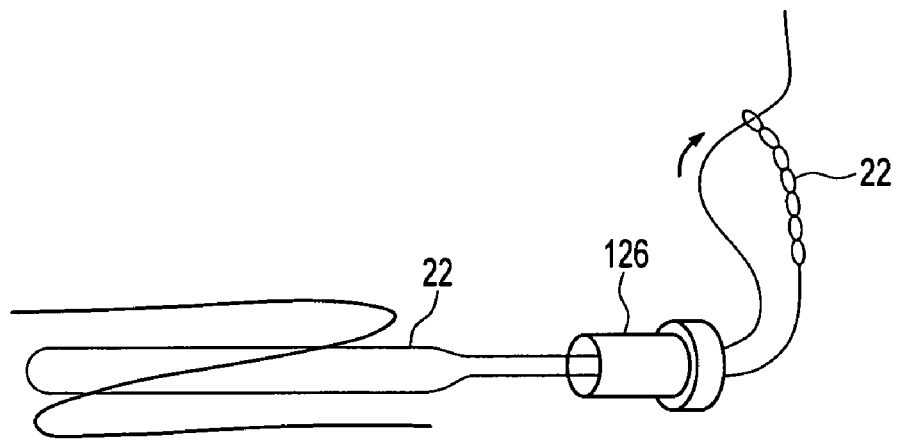
Figure 25C:
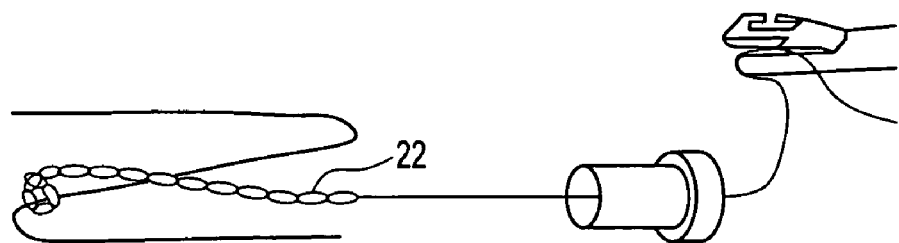
Figure 25D:
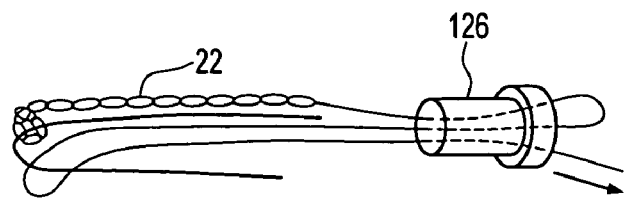
Figure 25E:
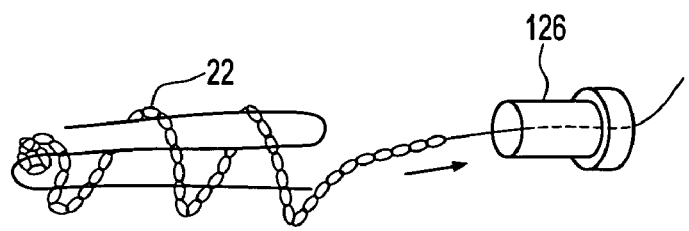
Figure 25F:
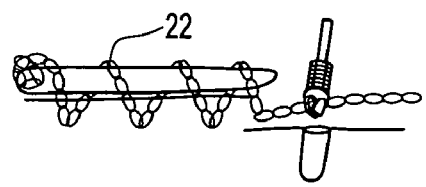
Figure 25G:
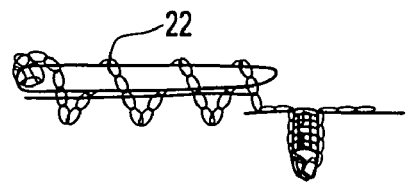

The suture chain of the present invention can also be used for knotless side-to-side suturing of U-shaped soft tissue defects (e.g., rotator cuff tears). Referring to FIG. 25A, the suture chain 22 of the present invention is passed through a U-shaped rotator cuff tear, near the apex of the tear, using a suture passing instrument such as the Scorpion sold by Arthrex, Inc. of Naples, Fla. As shown in FIG. 25B, outside of the cannula 126, the tail of the suture chain 22 is passed through the terminal link in the chain to fix the suture chain 22 to the apex of the tear. As shown in FIG. 25C, the tail of the suture chain 22 is then re-loaded into the Scorpion to pass through the opposite leaf of the U-shaped tear. Referring to FIG. 25D, the tail of suture chain 22 is passed through the rotator cuff, and the tail is then pulled to tighten suture chain 22 and pull the two leaves of the tear together. As shown in FIG. 25E, the above-described suture passage is repeated back and forth through the leaves of the rotator cuff. As shown in FIG. 25F, suture chain 22 is tensioned and secured to bone using an anchor, such as the swivel anchor described above, to complete the repair, as shown in FIG. 25G.

The above-described repair procedure, which can be performed with the suture chain of the present invention or regular suture strands, advantageously provides a knotless technique for margin convergence.

As described above, the suture chain of the present invention has application in surgical tissue repair, for example, in conjunction with one or more bone anchors. Tension on repair constructs is adjustable through selection of the chain link or links to be snagged by a bone anchor.

Other configurations included branched chains of two, three, or more individual chains radiating from a single intersecting link or several links. Each section of chain can be of uniform length with the others, or the chain sections can be a variety of lengths. Further configurations include strands or panels of two or more interlinked parallel chains forming a suturing device resembling chain mail. Multiple-ended suture chain configurations also are considered to be within the scope of the invention, without limitation.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of conducting arthroscopic surgery, comprising the steps of:
    providing a suture chain comprising a plurality of suture loops, at least one of the plurality of suture loops having a perimeter which is approximately equal to that of another of the plurality of suture loops, the suture chain being formed of a series of successive serial loops, wherein each of the plurality of suture loops is formed by lacing an end of the suture through itself a first time, thereby forming the loop and a junction, and then by lacing the end of the suture through itself a second time at the junction thereby creating an interlaced junction;
    securing one end of the suture chain to anchoring tissue with a first fixation device;
    capturing repair tissue with the suture chain; and
    approximating the captured repair tissue to the anchoring tissue by securing the other end of the suture chain to the anchoring tissue with a second fixation device.

2. The method of claim 1, wherein the suture chain is secured to the anchoring tissue with an anchoring device.

3. The method of claim 1, wherein the step of securing the one end of the suture chain to anchoring tissue comprises attaching the one end of the suture to a first anchor.

4. The method of claim 3, wherein the step of securing the other end of the suture chain further comprises attaching the other end of the suture to a second anchor.

5. The method of claim 1, wherein the repair tissue is a rotator cuff ligament.

6. A method of positioning tissue within a body, comprising the steps of:
    providing a suture chain formed of single suture comprising ultrahigh molecular weight polyethylene and comprising a plurality of suture loops, at least one of the plurality of suture loops having a perimeter which is approximately equal to that of another of the plurality of suture loops, the suture chain being formed of a series of successive serial loops with twice interlaced junctions between loops;
    positioning the suture chain in the vicinity of tissue to be treated; and
    securing the suture chain with a fixation device in the vicinity of the tissue.

7. The method of claim 6, wherein the fixation device is a swivel anchor.

\* \* \* \* \*